United States Patent [19]

Schmidt et al.

[11] Patent Number: 5,131,756
[45] Date of Patent: Jul. 21, 1992

[54] TEST CARRIER ANALYSIS DEVICE

[75] Inventors: Elmar Schmidt, Bruhl; Manfred Pauli, Schwetzingen, both of Fed. Rep. of Germany

[73] Assignee: Boehringer Mannheim GmbH, Mannheim, Fed. Rep. of Germany

[21] Appl. No.: 513,386

[22] Filed: Apr. 23, 1990

[30] Foreign Application Priority Data

Apr. 28, 1989 [DE] Fed. Rep. of Germany ....... 3914037

[51] Int. Cl.⁵ .......................................... G01N 21/47
[52] U.S. Cl. ...................................... 356/446; 356/39
[58] Field of Search ..................... 356/445, 446–448, 356/39, 420, 243; 250/250, 252.1 A

[56] References Cited

U.S. PATENT DOCUMENTS

| | | | |
|---|---|---|---|
| 3,473,878 | 10/1969 | Schweitzer | 356/210 |
| 3,910,701 | 10/1975 | Henderson | 356/39 |
| 4,518,259 | 5/1985 | Ward | 356/446 |
| 4,553,848 | 11/1985 | Rosicke et al. | 356/448 |
| 4,568,191 | 2/1986 | Barry | 356/446 |

FOREIGN PATENT DOCUMENTS

| | | |
|---|---|---|
| 0075766 | 9/1982 | European Pat. Off. . |
| 0165535 | 12/1985 | European Pat. Off. . |
| 8816390.3 | 8/1989 | Fed. Rep. of Germany . |

*Primary Examiner*—F. L. Evans
*Assistant Examiner*—K. P. Hantis
*Attorney, Agent, or Firm*—Nikaido, Marmelstein, Murray & Oram

[57] ABSTRACT

Test carrier analysis device for determining the reflectivity of a test field surface (measurement surface). An optical unit (2) of the device contains several light transmitters (6, 7) and a measurement receiver, and the light transmitters are directed obliquely from above onto the measurement surface. Improved accuracy without additional outlay is achieved by the fact that the light transmitters (6, 7) in the optical unit (2) are arranged opposite one another with off-set planes of incidence (28, 29).

13 Claims, 2 Drawing Sheets

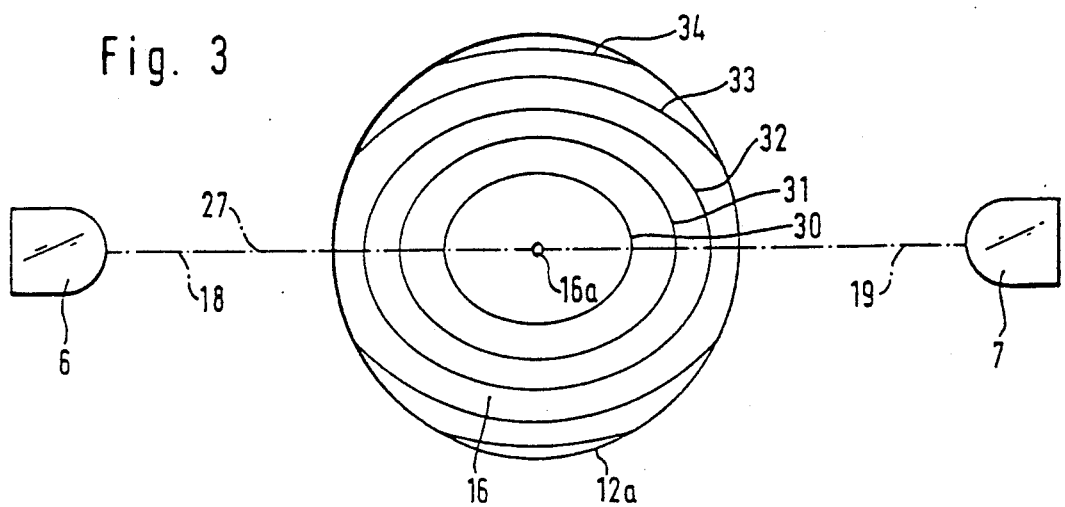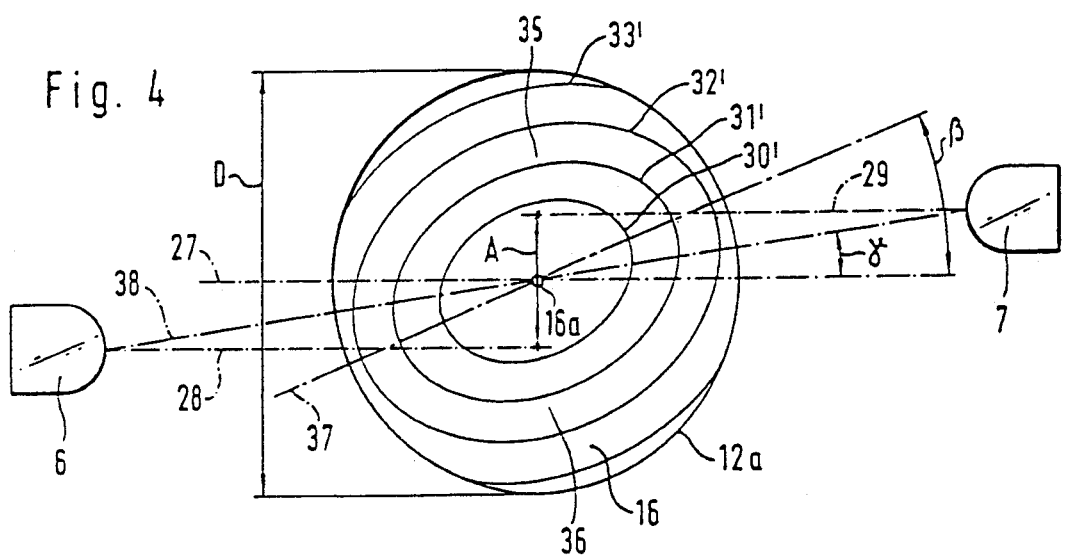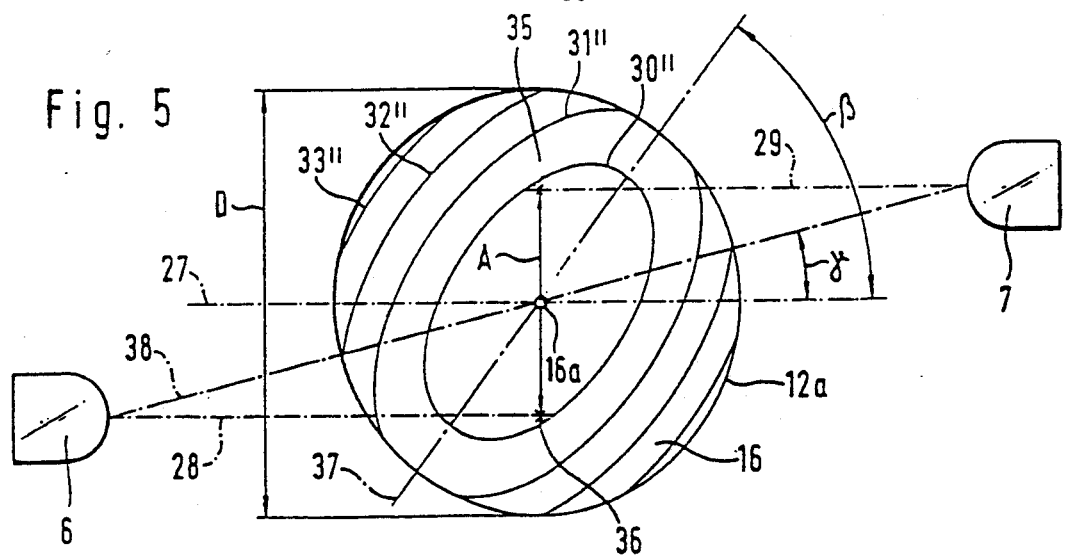

TEST CARRIER ANALYSIS DEVICE

The invention relates to a test carrier analysis device with an optical unit which contains several light transmitters, for illuminating the measurement surface of a test carrier, and a measurement receiver. The test carrier analysis device in addition comprises a measurement and evaluation circuit for measuring the output signal of the measurement receiver and for determining the reflectivity of the measurement surface.

Analyses of body fluids, in particular blood and urine, have been determined increasingly by means of so-called carrier-bonded tests in recent times. In these the reagents are embedded in corresponding layers of a solid test carrier, on which the sample is then placed. The reaction of the sample with the reagent system leads to a colour change on the test carrier. The test carriers mostly take the form of test strips, but other test carriers, for example in the form of square platelets, are also used.

The test carriers are often supplied with evaluation apparatuses, which, are designed to evaluate the color change by technical means and hence make a quantitative analysis possible. This usually takes place reflection-photometrically, i.e. the reflectivity (diffuse reflection) of the measurement surface is measured at one or more wave-lengths. The desired analysis result can be derived from the value for the reflectivity or else from the latter's variation in time.

High demands are thereby made of the accuracy of the reflection-photometric measurement. The demands are particularly high mainly because the variation of the reflectivity in the whole measurement range of the analysis is usually very small and consequently even small errors in the measurement of the reflectivity have a very marked effect on the analysis result. Despite these high accuracy requirements, test carrier analysis devices have to be small, manageable and cheap to manufacture, particularly as they are in many cases used for self-monitoring by patients (in particular diabetics) or for local applications in doctors' surgeries, rescue vehicles and similar.

The accuracy of the reflection measurement is dependent essentially on the measurement surface being illuminated with diffuse light. An Ulbricht globe, from which light impinges on the measurement surface uniformly from all directios in space, is particularly suitable for this purpose. Instead, use is increasingly made in test carrier analysis devices on cost grounds, and in order to make a small-scale unit possible, of several light transmitters which illuminate the measurement surface obliquely from above from different directions in space. The light sources used are usuallly light emitting diodes, which are distinguished by low energy use, low costs and high reliability. Such test carrier evaluation devices are described for example in EP-A 165 535 and in U.S. Pat. No. 4,518,259. Although the known devices are cheap and compact, their accuracy does not always match the particular requirements.

The object of the invention is to provide a test carrier analysis device with improved accuracy without additional structural outlay.

The object is achieved with a device of the kind described in the preamble by the fact that the light transmitters in the optical unit are arranged opposite one another with off-set planes of incidence.

The plane of incidence is the plane running vertical to the measurement surface and enclosing the optical axis of the respective light transmitter. The light transmitters are arranged in pairs, it being advisable that the light transmitters of a pair are of identical design, in particular have identical wave-lengths. The light transmitters of a pair illuminate the measurement surface in each case obliquely from above from opposite directions in space, it being preferable that they have the same angle of incidence to the measurement surface and are positioned the same distance from the latter. These conditions are also fulfilled With known devices (e.g. those known from the cited publications). There however, the light transmitters are always directed onto the same point, namely the centre of the measurement surface. The optical axes of two opposite light transmitters lie in the same plane of incidence. In the invention, contrastingly, they do not impinge onto the measurement surface at the same point. The planes of incidence are off-set relative to one other, and run approximately parallel to one other. This asymmetrical arrangement differs substantially from the usual method of construction. Surprisingly, however, the associated rotation of the illumination contours does not lead to disadvantages. Instead, a uniform diffuse illumination of considerably improved quality and hence improved accuracy of the measurement result is obtained.

A test carrier analysis device in which the optical axes of the light transmitters are not directed onto the same point is described in EP-A 99 024 (U.S. Pat. No. 4,568,191). No attempt is made there, however, to achieve a uniform illumination of the measurement field. The ray beams of the transmitters are rather superimposed in such a way that a deliberately non-unform illumination is obtained, with the aim of ensuring that in a particular operating range the measurement signal is independent of the distance between measurement receiver and measurement surface.

The invention will be described in detail below with reference to an exemplifying embodiment represented diagrammatically in the figures, where:

FIG. 3 shows the brightness contours in the measurement surface for a device according to the state of the art;

FIG. 4 and FIG. 5 show brightness contours according to FIG. 3 for two different forms of embodiment of a device according to the invention.

Figure 1:
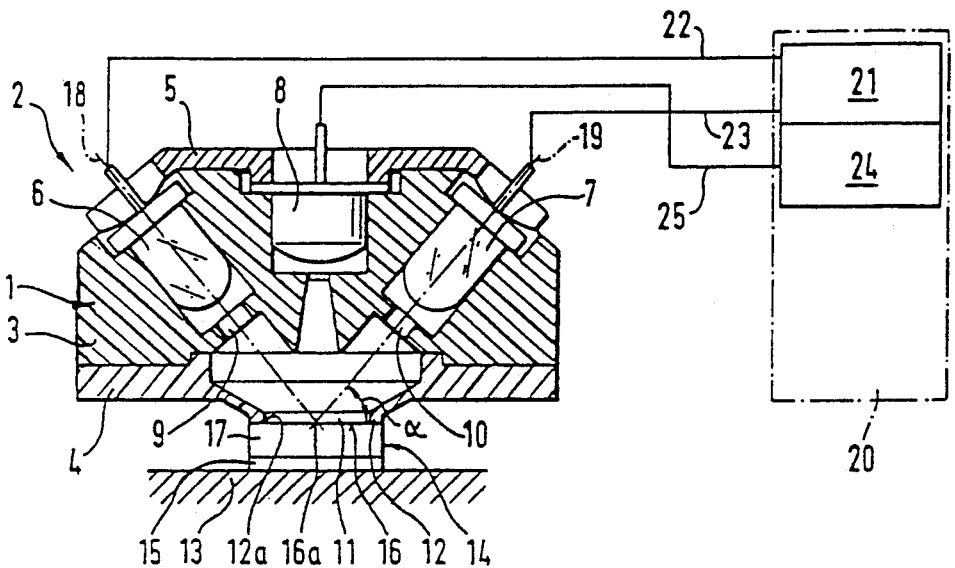
FIG. 1 shows the optical unit of a test carrier analysis device according to the invention in the section along the line I—I in FIG. 2 with attached diagram of the electronics.

The casing 1 of the optical unit 2 represented in FIG. 1 consists of a centre part 3, a bottom part 4 and a top part 5, which are appropriately made of plastics material. Two light emitting diodes 6, 7 as light transmitters and a photo-transistor 8 as measurement receiver are situated in matching recesses of the casing. The light of the light emitting diodes 6, 7 impinges through diaphragm openings 9, 10 onto the measurement window 11, which is framed by a diaphragm 12. The diaphragm 12 is an integral part of the bottom part 4, the whole of which is appropriately coloured dull black.

Below the window 11 there lies on a test carrier support 13 a test carrier 14. In the cross-sectional representation of FIG. 1 a base foil 15 can be distinguished to which a test field 17 is affixed. The surface of the test field 17 is framed by the diaphragm 12 and forms the measurement surface 16. The optical axes 18, 19 of the light transmitters 6, 7 impinge obliquely, i.e. at an angle, of incidence of less than 90°, onto the measurement surface 16. Preferred angles of incidence are between 30° and 60°.

The electronics unit of the test carrier analysis device is designated overall by 20. It contains a control unit 21 which activates the light emitting diodes 6, 7 via lines 22, 23. A measurement and evaluation circuit 24, likewise incorporated in the electronics unit 20, is connected to the measurement receiver 8 via line 25.

Suitable electronic circuitry is readily available to the skilled person. An example of a prior art device generally suitable for the instant invention is given in U.S. Pat. No. 4,553,848, the disclosure of which is hereby incorporated by reference.

Figure 2:
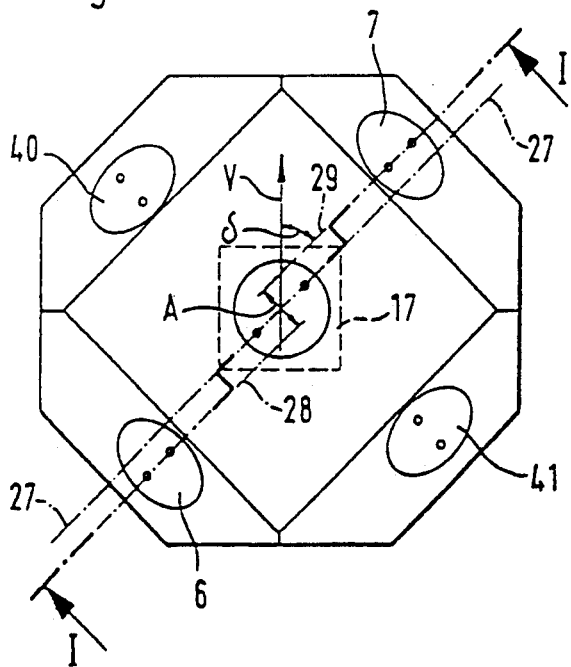
FIG. 2 is a top view onto an optical unit according to FIG. 1.

It can be seen from FIG. 2 that the light transmitters are not arranged with mirror symmetry, as is normally the case, but are off-set relative to the mid-plane 27, 28 and 29 represent the projections of the optical axes of the light transmitters onto the measurement surface plane or—expressed in a different way—the intersections of the respective planes of incidence with the measurement surface plane. They are off-set from one other by a distance A.

The effect of this measure will be explained in detail with reference to FIGS. 3-5.

In the arrangement according to FIG. 3 the optical axes 18, 19 of the light transmitters 6 and 7 coincide with the mid-plane 27, as has generally been the case to date. The optical axes of both light emitting diodes meet at the mid-point 16a of the measurement surface 16. The edge of the measurement surface 16 formed by the diaphragm 12 is marked 12a.

Within the measurement surface 16 are drawn lines of equal lighting intensity 30, 31, 32, 33, 34 on which the lighting intensity amounts to 90%, 80%, 70%, 60% and 50% of the intensity at the mid-point 16a. They are referred to below as brightness contours.

FIG. 4 shows a corresponding representation for the case where the planes of incidence 28, 29 of the light transmitters 6, 7 are off-set from one other by a distance A which corresponds to some 30% of the diameter of the measurement surface 16. The points of impact 35, 36 of the optical axes accordingly lie at a distance of A/2 from the mid-point 16a.

The brightness distribution, which is represented by the brightness contours 30', 31', 32', 33', is thereby rotated. The angle $\beta$ between the axis of symmetry 37 of the brightness distribution and the mid-plane 27 is more than twice as big as the angle $\alpha$ between the connecting line 38 of the light transmitters and the mid-plane 27. Despite this strong rotation a more uniform illumination is obtained. This effect is further reinforced if the distance A is further increased. FIG. 5 shows the brightness distribution for the case where A is about 55% of the diameter D. For the case where the measurement surface is not round, A should be referred to the greatest dimension of the measurement surface (i.e. the diagonal in the case of a square measurement surface, for example).

The distance by which the planes of incidence are off-set from one other should preferably be at least 20%, particularly preferably 30% and optimally at least 40% of the greatest dimension of the measurement surface.

In FIG. 5 the rotation of the axis of symmetry 37, characterised by the angle $\beta$, is even stronger than in FIG. 4. The illumination is however exceptionally uniform. This can be recognised by the fact that the brightness contours 30'', 31'', 32'', 33'' have a less elongate shape approximating more to a circle.

The improvement can be expressed quantitatively as the percentage of that surface on which the intensity is at least 80% of the intensity at the mid-point 16a. This percentage is approx. 39% for FIG. 3, approx. 46% for FIG. 4 and approx. 63% for FIG. 5. This more uniform illumination leads to an improved measurement accuracy, particularly in the cases often arising in practice where the measurement surface 16 exhibits inhomogeneity in the form of a centre-edge variation. It should be bore in mind here that the required blanking out of the measurement surface, measured by the measurement receiver leads in any case to an underestimation of the edge regions, a phenomenon which is further increased in the case of the illumination according to the state of the art.

If the structure of the test field has a preferred direction (V in FIG. 2), which is often the case given the continuous method of manufacturing the usual test field materials, the planes of incidence are preferably rotated, relative to the preferred direction V, by an angle which approximately compensates the angle $\beta$.

Idealised conditions are represented in the figures, in which the planes of incidence run exactly parallel to one another. Although this is generally advisable, slight deviations from this parallel arrangement are permissible without the advantages of the invention being forfeited. If the planes of incidence are not parallel, the distance A by which these are off-set from one other is referred to the points of contact 35, 36.

If light emitting diodes are used, slight deviations from the strict geometry represented in the figures are obtained simply because with these light sources the central ray of the light pencil generally does not coincide exactly with the optical axis of the arrangement (which is determined by the casing axis of the light emitting diode and the diaphragms 9, 10). Light emitting diodes "squint" to a certain extent. This results in a brightness distribution which is less symmetrical compared with the representation in FIGS. 4 and 5. Experiments show, however, that even in the real conditions produced by the imperfections of the light emitting diodes a substantially more uniform illumination is obtained on the basis of the invention.

The invention is not limited to the use of only two light emitting diodes. In particular it may be advisable to provide in an optical unit several pairs of light sources arranged opposite one other with off-set planes of incidence. In FIG. 2 there is represented a second pair of light emitting diodes 40, 41. The light emitting diodes of the various pairs have, appropriately, various wave-lengths, to enable multi-wave-length measurement of the reflectivity.

The reflectivity of a measurement surface is always determined by comparison with a reference surface. In the arrangement according to FIG. 1 this can take place, for example, by a reference field with a defined reflectivity being positioned beneath the measurement window 11 instead of the measurement field 15. If several light transmitters are used for the illumination of the same measurement surface, first of all the measurement surface and then the reference surface are usually illuminated with all the light transmitters, and the measurement results thereby obtained are compared to each other.

In the present invention it is however proposed according to a preferred embodiment that the measurement signals and the reference signals obtained on the measurement receiver during the illumination of the measurement surface and the reference surface with the light transmitters of a pair with equal wavelength (e.g. 6, 7) are compared with each other separately in order to obtain light-transmitter-specific interim results from which the reflectivity is calculated.

If the intensity signal of the measurement receiver 8, usually corrected for extraneous light and amplifier drift (cf. e.g. U.S. Pat. No. 4,553,848), is with illumination with the light emitting diode 6 designated as IP1 for the sample measurement and IR1 for the reference measurement and the corresponding signals for the light emitting diode 7 are designated as IP2 and IR2, light-transmitter-specific interim results R1, R2 are obtained, for example by quotient formation:

$$R_1 = \frac{I_{P1}}{I_{R1}} \qquad R_2 = \frac{I_{P2}}{I_{R2}}$$

The valid diffuse reflection value can then be determined algebraically, for example by simple unweighted calculation of the mean:

$$R = \frac{R_1 + R_2}{2}$$

In order to avoid multiple substitution of the actual test carrier with the measurement surface (sample measurement) for the reference surface (reference measurement), the values IP1 and IP2 or IR1 and IR2 are determined and stored in succession. Only after the measurement of all four values does processing in the manner stated above take place.

These preferred measures ensure that the measurement results of the individual light emitting diodes are weighted uniformly irrespective of their individual properties, whereas with simultaneous illumination of the measurement or reference surface with several light transmitters serious measurement errors are caused by the fact that the usual light emitting diodes, even if they are of exactly the same type, can have widely differing properties, particularly as regards their intensity, their wave-length and the preferred ray direction of the light pencil in relation to the casing axis. The sum effect of these factors can be such that the signal intensity arising on the receiver differs for one LED by a factor of 5 or more from another LED. This results in a completely non-uniform weighting of the signals obtained with the two light emitting diodes, which would be particularly disadvantageous in the case of the present invention because the light emitting diodes are directed onto different regions of the measurement surface 16.

What is claimed is:

1. A test carrier analysis device comprising an optical unit, which contains at least one pair of light transmitters and a measurement receiver, wherein the optical axes of the light transmitters run obliquely to a measurement surface, and means to measure the output signal of the measurement receiver, whereby determining the reflectivity of the measurement surface; characterized in that the light transmitters in the optical unit are arranged opposite one another with off-set planes of incidence.

2. A test carrier analysis device according to claim 1, characterized in that said light transmitters are light emitting diodes.

3. A test carrier analysis device according to claim 1, characterized in that the angles of incidence between the optical axes of the light transmitters and the measurement surface are between 30° and 60°.

4. A test carrier analysis device according to claim 1, characterized in that the distance by which said planes of incidence are off-set from one another is at least 20% of the greatest dimension of the measurement surface.

5. A test carrier analysis device according to claim 1, characterized in that the optical unit comprises more than one pair of light transmitters arranged opposite one another each with offset planes of incidence, said light transmitter pairs differing from each other with respect to their emitted wave-lengths.

6. A test carrier analysis device according to claim 1 including means to separately illuminate said measurement surface and a reference surface by each of said light transmitters and to receive the signals obtained thereby on said measurement receiver; means to separately compare the measurement surface and reference signals attributed to each light transmitter such as to obtain interim results which are light-transmitter-specific; and means to calculate the reflectivity of said measurement surface therefrom.

7. A test carrier analysis device according to claim 1, characterized in that the structure of the measurement surface has a preferred direction and the planes of incidence of said light transmitters are rotated about 30° to 60° with respect to said preferred direction.

8. A test carrier analysis device according to claim 1, characterized in that the distance by which the planes of incidence are off-set from one another is at least 30% of the greatest dimension of the measurement surface.

9. A test carrier analysis device according to claim 1, characterized in that the distance by which the planes of incidence are off-set from one another is at least 40% of the greatest dimension of the measurement surface.

10. A process of analyzing the reflectivity of a sample which comprises providing a test carrier analysis device, comprising an optical unit, which contains at least one pair of light transmitters and a measurement receiver, wherein the optical axes of the light transmitters are arranged opposite one another with offset planes of incidence and run obliquely to a measurement surface of the sample, and means to measure the output signal of the measurement receiver, providing a reference surface of known reflectivity available to said light transmitters; illuminating said reference surface and said measurement surface of said test carrier analysis device with each of said light transmitters, whereby obtaining signals from said surfaces respectively; comparing said signals individually for each of said light transmitters, whereby obtaining an interim reflectance value specific to each of said light transmitters; and determining the reflectance of said measurement surface from the interim reflectance values.

11. The process claimed in claim 10 including using two pairs of light transmitters each pair of which transmitting a different wave length.

12. A process of analyzing the reflectivity of a sample which comprises providing a test carrier analysis device, comprising an optical unit, which contains at least one pair of light transmitters and a measurement receiver, wherein the optical axis of the light transmitters are arranged opposite one another with offset planes of incidence and run obliquely to a measurement surface of the sample, and means to measure the output signal of the measurement receiver, simultaneously impinging light from at least one pair of said offset light transmitters on said surface of said sample; collecting light reflected from said surface by a receiver, whereby generating an output signal therefrom; and converting said output signal into a reflectivity measurement.

13. A process as claimed in claim 12 including sequentially impinging light on said surface from at least two pairs of light transmitters, each pair emitting a different wave length.

* * * * *

UNITED STATES PATENT AND TRADEMARK OFFICE
CERTIFICATE OF CORRECTION

PATENT NO. : 5,131,756

DATED : July 21, 1992

INVENTOR(S) : SCHMIDT et al

It is certified that error appears in the above-identified patent and that said Letters Patent is hereby corrected as shown below:

On the title page, in item [30] Foreign Application Priority Data correct the Priority Document No. from "3914037" to —3914037.7—.

Signed and Sealed this

Twenty-eighth Day of September, 1993

Attest:

BRUCE LEHMAN

Attesting Officer

Commissioner of Patents and Trademarks